(12) United States Patent
Nazabal et al.

(10) Patent No.: US 8,097,427 B2
(45) Date of Patent: Jan. 17, 2012

(54) DIRECT MASS SPECTROMETRIC ANALYSIS OF DRUG CANDIDATES TARGETING PROTEIN COMPLEXES

(75) Inventors: Alexis Txomin Nazabal, Zürich (CH); Ryan Jay Wenzel, Melrose, MA (US)

(73) Assignee: CovalX AG, Zurich (CH)

( * ) Notice: Subject to any disclaimer, the term of this patent is extended or adjusted under 35 U.S.C. 154(b) by 332 days.

(21) Appl. No.: 12/450,204

(22) PCT Filed: Mar. 14, 2008

(86) PCT No.: PCT/EP2008/053085
§ 371 (c)(1),
(2), (4) Date: Sep. 16, 2009

(87) PCT Pub. No.: WO2008/113758
PCT Pub. Date: Sep. 25, 2008

(65) Prior Publication Data
US 2010/0099200 A1    Apr. 22, 2010

(30) Foreign Application Priority Data

Mar. 16, 2007  (EP) .................................... 07104314

(51) Int. Cl.
*G01N 33/53*  (2006.01)
*G01N 31/00*  (2006.01)
(52) U.S. Cl. ......... 435/7.21; 435/4; 435/7.1; 435/287.9; 436/501; 436/518; 436/525; 436/529; 436/535; 436/809; 427/287; 427/337; 427/338; 530/300; 530/350

(58) Field of Classification Search ........................ None
See application file for complete search history.

(56) References Cited

FOREIGN PATENT DOCUMENTS
WO      2006/116893      11/2006

OTHER PUBLICATIONS

International Search Report issued Aug. 25, 2008 in International (PCT) Application No. PCT/EP2008/053085.
Alexis Nazabal et al., "Immunoassays with Direct Mass Spectrometric Detection", Analytical Chemistry, vol. 78, No. 11, XP002438305, pp. 3562-3570, Jun. 1, 2006.
Sarah Sanglier et al., "Monitoring ligand-mediated nuclear receptor-coregulator interactions by noncovalent mass Spectrometry", European Journal of Biochemistry, vol. 271, No. 23-24, XP002438304, pp. 4958-4967, Dec. 2004.
Gera'ld Bolbach, "Matrix-Assisted Laser Desorption/Ionization Analysis of Non-Covalent Complexes: Fundamentals and Applications", Current Pharmaceutical Design, vol. 11, No. 20, XP008077825, pp. 2535-2557, 2005.

*Primary Examiner* — Lisa Cook
(74) *Attorney, Agent, or Firm* — Wenderoth Lind & Ponack, L.L.P.

(57) ABSTRACT

The invention relates to a method of using high mass matrix assisted laser desorption-ionization (MALDI) mass spectrometry for the qualitative and quantitative analysis of the effect of drug candidates on protein complexes such as protein-protein interactions in purified samples or complex biological matrices, as well as to the use of this method for lead compound optimization, drug characterization, drug manufacturing processes, and drug quality control processes, including automated high throughput applications.

13 Claims, 6 Drawing Sheets

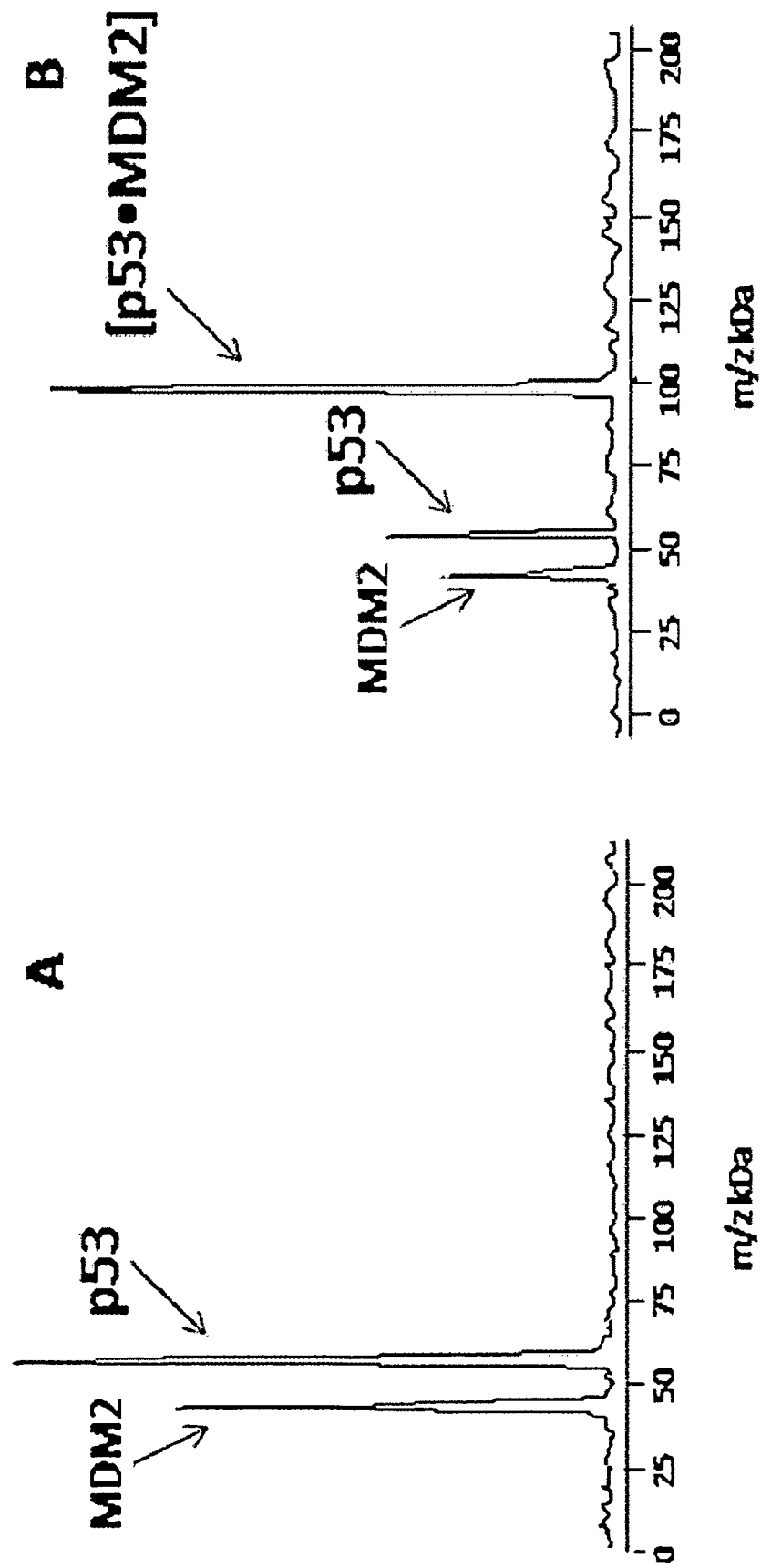
Fig. 4 A, B

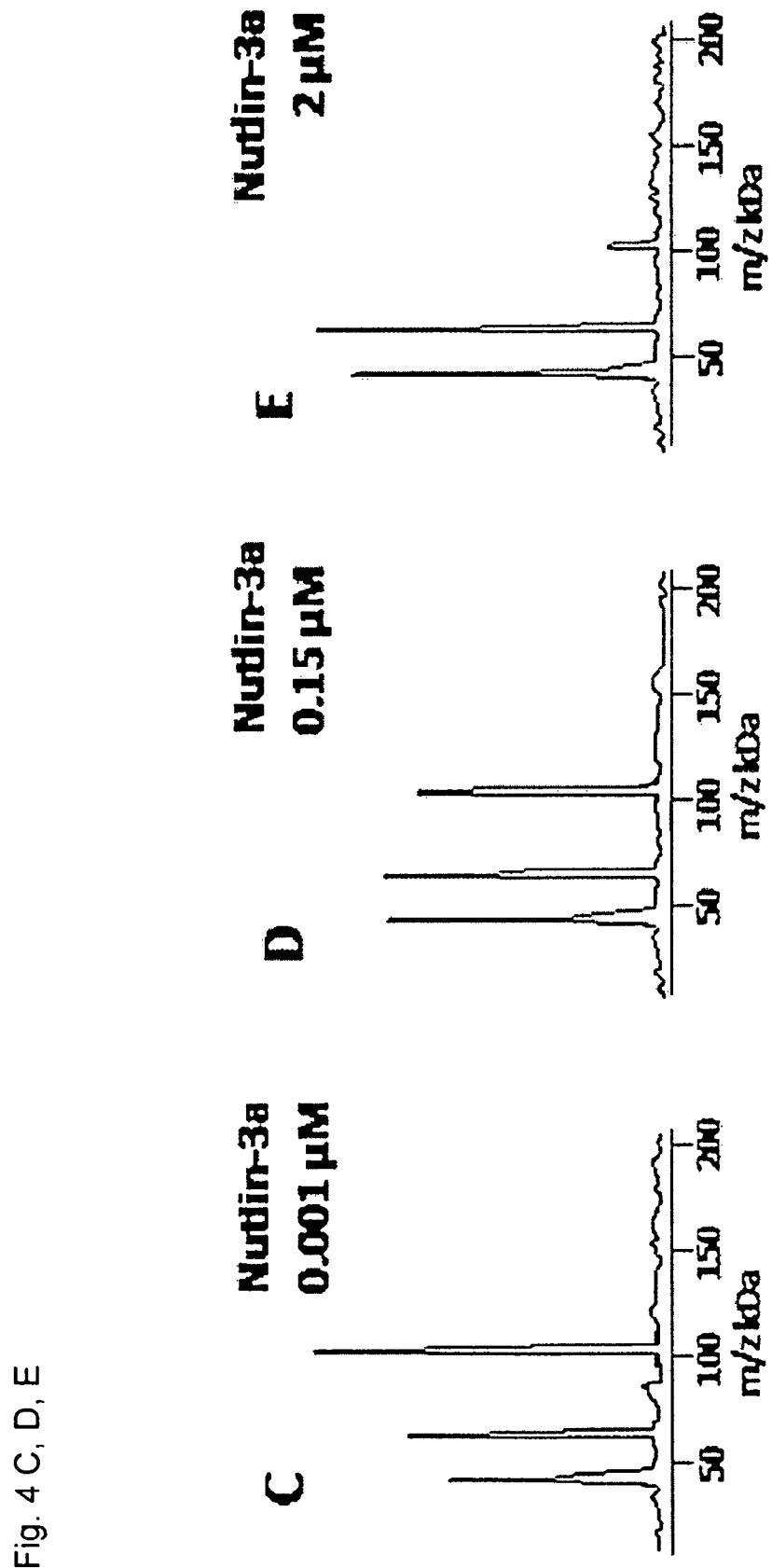
Fig. 4 C, D, E

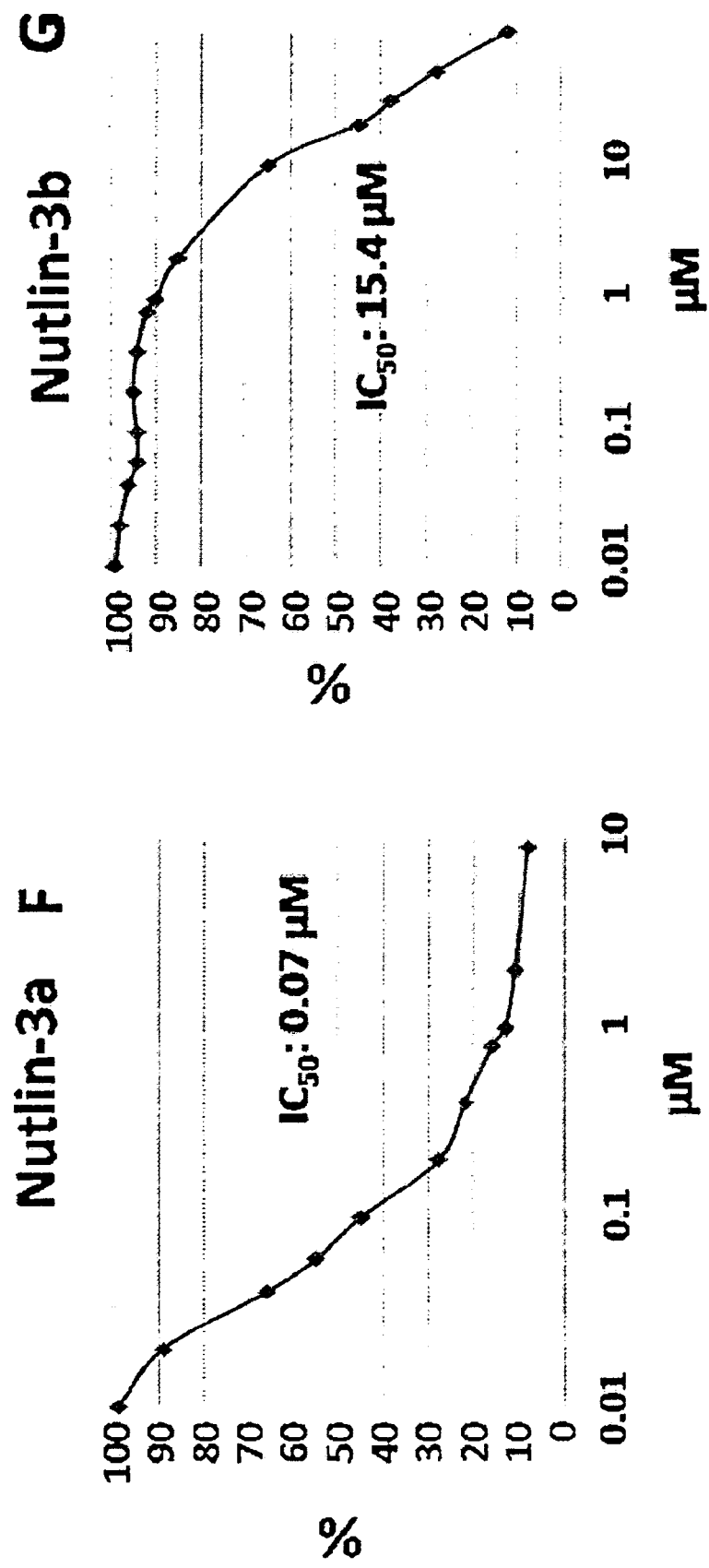
Fig. 4 F, G

DIRECT MASS SPECTROMETRIC ANALYSIS OF DRUG CANDIDATES TARGETING PROTEIN COMPLEXES

This application is a 371 of PCT/EP2008/053085 filed Mar. 14, 2008 and foreign application EPO 07104314.5 filed Mar. 16, 2007.

FIELD OF THE INVENTION

The present invention relates to a method of analyzing the effect of drug candidates targeting protein complexes using MALDI mass spectrometry combined with chemical cross-linking. The effect may be quantified and given as a $IC_{50}$ value against the targeted protein complex.

BACKGROUND OF THE INVENTION

Protein-protein interactions play a central role in physiology. In cells, proteins are organized in a complicated and flexible network that can be regulated to ensure almost all cellular processes. When drugs are targeting proteins, they in fact affect the entire networks the targeted protein belongs to, having effects on protein-protein interactions. The direct analysis of the effect of drug candidates on protein-protein interactions or protein complexes is extremely important during the pre-clinical stage of drug discovery when hundreds of potential "lead compounds" must be investigated.

Drug candidates may take the form of small molecules (typically with MW<1000 Da), recombinant proteins, recombinant peptides, antibodies or antibody fragments. After screening of a drug candidate library, the in-depth characterization of the potential therapeutic molecules is crucial for the pre-clinical selection process of lead compounds. This selection process ensures that the best candidates enter the costly clinical process and that the bad or useless candidates are rejected as early as possible in the drug discovery process.

Conventional technologies for characterizing interactions between drugs and proteins include ELISA (Enzyme Linked Immunosorbant Assay) type assays, radioimmunoassay and related techniques and Surface Plasmon Resonance technology (SPR). Among these technologies, SPR is the only one able to characterize "in depth" the interaction between drugs and proteins by measuring binding kinetics, dissociation and association constants and the nature of a target-ligand interaction.

Mass spectrometry is a standard tool for the analysis of proteins after the introduction of the so-called "soft ionization" method, including Electrospray Ionization (ESI) and Matrix Assisted Laser Desorption Ionization (MALDI). These ionization methods have been developed to analyze large molecular weight biopolymers (Fenn et al., Science 246:64-71, 1989; Karas and Hillenkamp, Anal. Chem. 60:2299-3001, 1988). Although mass spectrometry is a standard tool for the analysis of proteins, it is still challenging to use this technology for the analysis of protein-protein interactions and protein complexes. The main difficulty is the tendency of non-covalent interactions between proteins to dissociate during the analysis.

Electrospray ionization (ESI) is the preferred method for the analysis of intact protein complexes as the sample can be analyzed in the presence of favorable buffers, maintaining the interactions stable (Loo, Int. J. Mass Spectrom. 200(1):175-186, 2000). Electrospray ionization mass spectrometry has been used for the analysis of the complex formed between drug candidates Sch 54292, Sch 54341 and Sch 53721 when incubated with the protein ras-GDP (Pramanik et al., J. Mass Spectrom. 33:911-920, 1998). This ionization method has also been used for the analysis of the complexes formed between DNA and small molecules (nogalamycin, hedamycin and distamycin) (Beck et al., Mass Spectrom. Rev. 20:61-87, 2001). Sanglier S. et al., Eur. J. Biochem. 271:4958-4967, 2004 describe the use of ESI-MS for the measurement of ternary complexes resulting from the retinoid corepressor nuclear receptors box peptides interaction with the ligand binding domain of the retinoic acid/retinoid X receptor heterodimer. Finding the favourable conditions to observe intact ions from protein complexes using electrospray ionization is time consuming and still a major difficulty. The major issue when using ESI-MS for determining equilibrium association of non covalent complexes is the difference of response factors for these complexes during ESI ionization that can be due to the collisional activation in the source of the mass spectrometer. Discrimination processes (e.g. mass-dependent ionization efficiency, mass-dependent ion transmission through the mass spectrometer, and non-uniform response of the detector) do not generally allow relating the ion intensities of different species to their solution concentrations. These properties of ESI ionization have major consequences in the case of competition experiments as the response factor for the complexes interacting with different drugs is different (Gabelica, V. et al. J. Mass Spectrom. 38: 491-501, 2003).

Only few studies have been reported for the analysis of intact protein complexes using MALDI ToF mass spectrometry. The main reasons are that non-covalent complexes can dissociate easily not only during the ionization process with laser desorption but also during sample preparation (MALDI-MS; reviewed in Nordhoff et al., Mass Spectrom. Rev. 15:67-138, 1997). Another issue is the ability of a standard MALDI mass spectrometer to detect the intact high-mass protein complexes as MALDI generates mostly single charged pseudo molecular ions. MALDI mass spectrometry has been used for the analysis of intact non-covalent protein complexes using a combination of high-mass detection and cross-linking chemistry (Nazabal, A. et al., Anal Chem. 78:3562-3570, 2006). This analytical method has never been applied to the analysis of drugs targeting protein-protein interactions and protein complexes. MALDI cumulates several disadvantages for this analysis: 1) The laser used for the ionization disrupts the targeted protein complex; 2) The detection sensitivity is reduced or inexistent in the high-mass range; 3) The presence of small molecules in the sample is reducing the ability to detect the high-molecular weight macromolecules because of selective ionization phenomenon; 4) MALDI mass spectrometry is not considered a quantitative tool. There is no direct correlation between the intensity of a peak detected and the amount of protein complexes in a sample.

In WO 2006/116893 (Eidgenössische Technische Hochschule Zürich) a mass spectrometric method is proposed wherein intact ions of undigested, unfragmented covalently stabilized supramolecular target-ligand complexes are analysed with matrix assisted laser desorption ionisation (MALDI). The method is illustrated by the analysis of antibody-antigen complexes and other protein-protein complexes such as complexes between CDC42 and *Salmonella* outer protein SopE but has never been used for the quantitative analysis of drug candidates targeting protein complexes.

SUMMARY OF THE INVENTION

It is an object of the present invention to provide a method of detection and determination of the effect of drug candidates on protein complexes by incubating drug candidates with the protein complex in either purified multi-component samples or heterogeneous biological matrices and subsequently cross-linking the interacting partners to form covalently stabilized protein complexes and finally analysing the stabilized protein complexes with MALDI ToF mass spectrometry equipped for high mass detection without digestion or fragmentation of the sample.

In particular, the present invention provides a method of determining the effect of drug candidates on protein complexes by measuring intact ions of undigested, unfragmented protein complexes using mass spectrometry comprising the steps of:
(a) incubating a targeted protein complex with a drug candidate;
(b) contacting the targeted protein complex in presence of the drug candidate with a cross-linking reagent to form a covalently stabilized protein complex;
(c) analyzing the intact ions formed by high mass MALDI ToF mass spectrometry equipped with a high mass detector;
(d) determining directly the effect of the drug candidate on the targeted protein complex by comparing the mass peaks obtained for the targeted protein complex in presence of the drug candidate with the mass peaks obtained in presence of a negative control molecule.

If in step (a) the incubation is done with different concentrations of the drug candidate, the effect can be quantified in step (d) for different concentrations and represented, for example, as an $IC_{50}$ value of the drug candidate for the targeted protein complex.

The present invention further provides the use of this method as a very versatile tool in various applications such as lead compound optimization, drug development, characterization of protein biopharmaceuticals such as antibodies or other therapeutic proteins and peptides, drug manufacturing and quality control, including automated and/or high throughput applications.

BRIEF DESCRIPTION OF THE FIGURES

FIG. 4: Determination of the $IC_{50}$ values for inhibitors Nutlin-3a and Nutlin-3b against the protein complex MDM2-p53. (A, B): Analysis of the MDM2-p53 interaction using High-Mass MALDI mass spectrometry combined with chemical cross-linking. (C, D, E): Analysis of the interaction MDM2-p53 after treatment with different concentrations of Nutlin-3a. (F, G): Determination of $IC_{50}$ values for Nutlin-3a and Nutlin-3b against MDM2-p53 interaction.

DETAILED DESCRIPTION OF THE INVENTION

Figure 1:
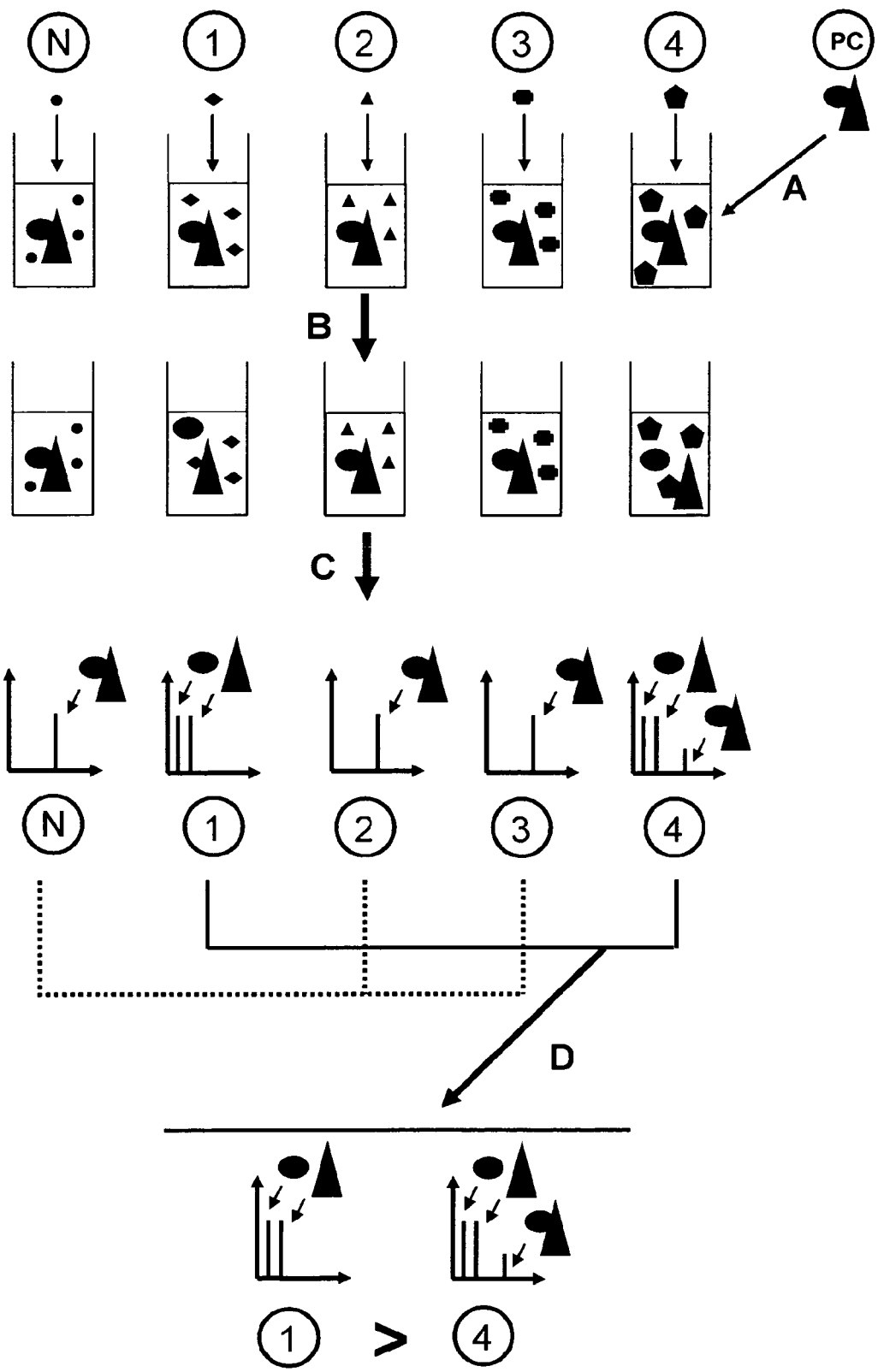
FIG. 1: Basic overview of method for analysing the effect of drug candidates on protein-protein interactions or protein complexes according to the invention. In a first step (A) drug candidates (1, 2, 3, 4) or a negative control molecule (N) are mixed with the targeted protein complex (PC). After incubation (B), mixing with the cross-linking reagent and high-mass MALDI ToF mass spectrometry analysis (C), the mass peak area of the peak corresponding to the protein complex is calculated and compared for the experiments with each drug candidates and for the experiment with the negative control. 2 and 3 have no effect on the targeted protein complex. In contrast, 1 and 4 have a disruptive effect on the targeted protein complex. By comparing the mass peak area of the peak corresponding to the targeted protein complex after incubation with the drug candidates 1 and 4, it is possible to rank (D) the effect of these molecules, i.e. 1>4 in the particular example.

The present invention relates to a method of analyzing the effect of drug candidates such as small molecule compounds (MW<1000 Da), antibodies, antibody fragments and other therapeutic proteins and peptides on protein complexes in either purified multicomponent mixtures or heterogeneous biological matrices with high sensitivity and accuracy using the combination of high mass MALDI ToF mass spectrometry and cross-linking chemistry for a robust and routine analysis.

In particular, the method of the present application allows to determine the effect of drug candidates on protein complexes, for example protein-protein interaction complexes, with high sensitivity and accuracy by first incubating the drug candidate with the targeted protein complex sample and subsequently cross-linking specifically the protein complex sample containing the drug candidate and subjecting it to MALDI ToF mass spectrometry using sensitive high mass detection with no digestion or fragmentation step. The effect of drug candidates on the protein complex is determined directly from the MALDI mass spectrum obtained by comparing the peak area of the protein complex detected in presence of the drug candidate versus the peak area of the protein complex in presence of a negative control. The present invention demonstrates that it is possible to establish a correlation between the efficiency of a drug candidate to disrupt or facilitate a protein interaction within a protein complex, i.e. the affinity of a drug candidate for a protein-protein interaction or other protein interaction within a complex, and the mass peak area of the peaks detected for the protein complex in the sample analyzed.

In a specific embodiment the effect of a drug candidate on a protein complex is analyzed in either purified multi-component samples or heterogeneous biological matrices with no digestion or fragmentation step.

In a further specific embodiment, the drug candidates represent small molecule compounds (MW<1000 Da), antibodies, antibody fragments, and other therapeutic proteins and peptides.

The method of the present invention provides for a direct mass analysis of the effect of drug candidates on protein complexes such as protein-protein interaction complexes with no digestion or fragmentation, and thus also includes the ability to select suitable drug candidates and rank drug candidates for their relative effect on protein complexes.

The use of the method of the present invention allows not only a direct determination of the effect of a drug candidate on a protein complex, but also the quantification of the effect detected, for example as an $IC_{50}$ value. This is a particular important aspect of the invention, since state of the art technologies are not suitable for quantitative determination of drug candidate—protein complex interactions.

The invention itself will best be understood from the following description of the preferred embodiments of the present invention. It is understood that those skilled in the art may conceive modifications and/or variations to the specific embodiments shown and described herein. Any such modifications or variations that fall within the purview of this description are intended to be included therein as well. The description of preferred embodiments and best mode of the invention known to the applicant at the time of filing the application are presented and are intended for the purposes of illustration and description. It is not intended to be exhaustive or to limit the invention to the precise form disclosed, and many modifications and variations are possible in the light of the teachings above and below. The embodiments demonstrate the principles of the invention and its practical applications and enable others skilled in the art to best utilize the invention in various embodiments and with various modifications as are suited to the particular use contemplated.

The method of the present invention allows the direct determination of the effect of drug candidates on protein complexes, e.g. from either purified protein complex samples or heterogeneous biological matrices, using high mass MALDI ToF mass spectrometry and crosslinking chemistry.

The method of the present invention is based on the finding that the analysis of protein complex samples incubated with drug candidates is possible after cross-linking, e.g. in either purified sample or heterogeneous biological matrices. MALDI mass spectrometry allows the direct determination of the effect of the drug candidate on the protein complex. There is a correlation between the mass peak area of the peaks detected by MALDI mass spectrometry for the targeted protein complex in the presence or absence of the drug candidate and the effect of the drug candidate on the protein complex targeted.

The present invention provides a direct method for determining the effect of drug candidates on protein complexes and comprises the steps of:
(a) incubating a drug candidate with one part of the protein sample containing the targeted protein complex and incubating a negative control molecule with another part of the protein sample containing the targeted protein complex;
(b) contacting the samples from step (a) containing the drug candidate and the negative control molecule, respectively, and the targeted protein complex with a crosslinking reagent or a crosslinking reagent mixture to form a covalently stabilized protein complex;
(c) analyzing the intact ions formed from the protein complex of step (b) by high mass MALDI ToF mass spectrometry equipped with a high mass detector;
(d) determining directly the effect of the drug candidate by comparing the mass peaks for the targeted protein complex from the sample comprising the drug candidate and from the sample comprising the negative control molecule.

If any of the procedures or partial steps described and claimed could be regarded as being practised on the human or animal body, such practise on the human or animal body is herewith expressly excluded.

The negative control is obtained by incubating the targeted protein complex with a small molecule, an antibody, a fragment antibody or a therapeutic protein or peptide that is known or determined to have no effect on the protein complex targeted. The negative control molecule is chosen such that it is comparable in structure and molecular weight to the drug candidate. For example, if the drug candidates are small molecule compounds with a molecular weight below 1000 Da, the negative control molecule is also a small molecule with similar molecular weight and belonging to the same or a related chemical class or grouping, such that unspecific interactions with the protein complex or with other components in the protein complex sample are comparable. Likewise, if the drug candidates are antibodies or antibody fragments, the negative control molecule is also an antibody or antibody fragment, respectively, preferably of the same Ig or fragment class, but having a different specificity, and in particular no specificity for the targeted protein complex. If the drug candidates are therapeutic proteins or peptides, the negative control molecule is also a protein or peptide with similar molecular weight and similar tertiary structure, such that unspecific interactions with the protein complex and with other components in the protein complex sample are comparable.

After cross-linking of the protein complex sample in presence of the drug candidate or of the negative control molecule, the sample is analyzed by high mass MALDI ToF mass spectrometry. For that purpose, the crosslinked mixture is mixed with a suitable matrix leading to co-crystallization with the matrix and thereby freezing and stabilizing the protein complexes. The peak areas for the targeted protein complex incubated with the negative control molecule are compared with the peak areas detected after direct analysis of the protein complex without any incubation. The peak areas are expected to be the same or almost the same. Differences in the peak areas found reflect unspecific interactions occurring between the negative control molecule and the targeted protein complex.

The present invention provides a method to quantitatively determine the interaction of drug candidates on targeted protein complexes, for example by determination of a $IC_{50}$ value. When two drug candidates have an effect on a protein complex, such as disrupting or facilitating association, it is likewise possible to determine quantitatively this effect. The effect of the drug candidate on the protein complex may be established based on the total mass peak area of the peaks corresponding to the protein complex and peaks corresponding to the separate subunits of the protein complex in the same mass spectrometry spectrum. The $IC_{50}$ value of a drug candidate is then determined by plotting the percentage of the complex still present in the mixture as a function of the concentration of inhibitor present in the sample.

If the cross-linking step is omitted the high mass MALDI ToF mass spectrometry of the protein complex sample pre-incubated with the drug candidate corresponds to a sample containing the different subunits of the protein complex. The intact protein complex can not be detected because it falls apart into its subunits under the conditions of high mass MALDI ToF mass spectrometry.

More particularly, the method of determining the effect of drug candidates on protein complexes by measuring intact ions of an undigested, unfragmented protein complex pre-incubated with drug candidates comprises the steps of:
(a) incubating a targeted protein complex sample with a negative control molecule or a drug candidate;
(b) contacting said first sample from step (a) with a cross-linking reagent or cross-linking reagent mixture to obtain a second sample containing the covalently stabilized protein complex,
(c) mixing said second sample from step (b) with a matrix solution to obtain a sample/matrix mixture;
(d) depositing said sample/matrix mixture on a substrate, thereby forming a homogeneous, thin layer;
(e) illuminating the sample/matrix mixture with radiation from a laser whereby said protein complex covalently stabilized is desorbed and intact ions are generated;
(f) mass separating and detecting said intact ions of the undigested, unfragmented covalently stabilized protein complex using a mass separation and a high mass detection system;

(g) determining the mass peak area of the peaks measured for the protein complex detected;
(h) comparing the value for the mass peak area of the peak corresponding to the protein complex obtained after incubation of the protein complex with the drug candidate with the value for the mass peak area of the peak corresponding to the protein complex obtained after incubation with the negative control molecule;
(i) determining from the comparison the effect of the drug candidate on the targeted protein complex.

In a particular embodiment, the method of determining the effect of drug candidates on protein complexes by measuring intact ions of an undigested, unfragmented protein complex pre-incubated with drug candidates comprises the steps of:
(a) incubating a targeted protein complex sample with several different concentrations of a drug candidate and a negative control molecule;
(b) contacting said first series of samples from step (a) with a cross-linking reagent or cross-linking reagent mixture to obtain a second series of samples containing the covalently stabilized protein complex,
(c) mixing said second series of samples from step (b) with a matrix solution to obtain a sample/matrix mixture;
(d) depositing said sample/matrix mixtures on a substrate, thereby forming a homogeneous, thin layer;
(e) illuminating the sample/matrix mixtures with radiation from a laser whereby said protein complex covalently stabilized is desorbed and intact ions are generated;
(f) mass separating and detecting said intact ions of the undigested, unfragmented covalently stabilized protein complex using a mass separation and a high mass detection system;
(g) determining the mass peak area of the peaks measured for the protein complex detected;
(h) comparing the value for the mass peak area of the peak corresponding to the protein complex obtained after incubation of the protein complex with different concentrations of the drug candidate with the value for the mass peak area of the peak corresponding to the protein complex obtained after incubation with the negative control molecule;
(i) determining from the comparison the percentage of protein complex having been present after incubation in step (a),
(j) determining the $IC_{50}$ value of the drug candidate against the target by plotting the percentage determined in step (i) as a function of the concentration of the drug candidate.

As used herein, the term "drug candidate" refers to small organic molecules (typically with a molecular weight below 1000 Da), antibodies, antibody fragments and therapeutic proteins and peptides. The small molecules may belong to any chemical class suspected to interact with a protein complex and expected to be pharmaceutically acceptable. Antibodies may belong to any of the immunoglobulin (Ig) classes, e.g. IgA, IgD, IgE, IgG or IgM, and may be polyclonal, monoclonal, genetically engineered, e.g. humanized, or otherwise adapted to a particular use. Antibody fragment may be e.g. a heavy chain, light chain, Fab or Fc fragment, or single chain fragment, such as scFv. Therapeutic proteins or peptides may be any protein or peptide in its natural, modified natural or fully recombinant form. "Therapeutic" means that it is expected to have a beneficial effect when applied as a drug and is regarded as pharmaceutically acceptable.

As used herein the term "protein complex" refers to complexes arising from the specific binding of a protein with a binding partner, wherein said binding partner can be one particular or a plurality of proteins, nucleic acids, synthetic organic compounds or particles and the like, to form said protein complexes such as protein-protein, protein-nucleic acid, protein-drug, protein-viral particles, antibody-antigen, substrate-enzyme complexes and the like. Within this definition protein complex also comprises protein-protein interactions, e.g. interactions between different proteins, or dimers, trimers, tetramers or higher oligomers of the same protein. Interactions between subunits of protein complexes are usually non-binding interactions, such as those interactions caused by hydrogen bridges, pi electron systems such as (optionally conjugated) C—C double bonds or aromatic rings, e.g. phenyl, and heteroaromatic rings, e.g. pyrrole, imidazole, indole, pyrimidine or purine rings, and interactions between metal atoms and oxygen, nitrogen or sulfur atoms, but may also be weak, and in particular reversible, covalent binding interactions, e.g. sulfur-sulfur bridges.

As used herein, the term "effect of drug" refers to the binding, dissociation or association effect of drug candidates on the protein complex targeted. This effect is monitored by integrating the mass peak area of the peak corresponding to the protein complex after incubation of the drug candidate compared with the mass peak area of the same peak after incubation of a negative control molecule.

As used herein, the term "high mass MALDI mass spectrometry" refers to analysis using a matrix assisted laser desorption ionization mass spectrometer instrument specially modified to enhance the sensitivity of detection of ions in the high-molecular range, e.g. ranging from about 5 kDa to about 100 MDa, more specifically from about 10 kDa to about 20 MDa, most preferably from about 40 kDa to about 10 MDa, whatever the technology applied to perform this enhancement is.

As used herein, the term "intact ions" refers to charged molecules created for mass analysis from the protein complex, i.e. the covalently stabilized aggregates, without proteolysis, degradation or dissociation of the protein complex before or during mass analysis.

As used herein, the term "covalently stabilized protein complexes" refers to protein complexes as defined above, which have been cross-linked by any known or as yet undiscovered means without disturbing the stoichiometry of the protein complex.

As used herein, the term "purified sample" refers to any sample containing a heterogeneous or homogeneous mixture of proteins, polypeptides, glycopolypeptides, antibodies, phosphopolypeptides, peptidoglycans, polysaccharides, peptidomimetics, lipids, carbohydrates, polynucleotides or organic compounds, which has been purified in part or completely.

As used herein, the term "heterogeneous biological matrices" refers to any crude reaction mixture including mixtures obtained from dissolution of a solid material such as a tissue, cells, or a cell pellet; biological fluid such as urine, blood, saliva, amniotic fluid, or an exudate from a region of infection or inflammation; a cell extract, or biopsy sample; or mixtures obtained from a living source, for example, from an animal such as a human or other mammal, a plant, a bacterium, a fungus or a virus.

As used herein, the term "high or higher mass" with reference to protein complexes refers to a mass higher than about 10 kDa, e.g. ranging from about 10 kDa to about 100 MDa, more specifically from about 20 kDa to about 20 MDa, most preferably from about 40 kDa to about 10 MDa.

As used herein, the term "analyze" means to identify or detect the presence, absence or change of, or determine the identity of such covalently stabilized protein complexes after incubation with the drug candidate or the negative control molecule.

As used herein, the term "high throughput" means to conduct more than one analysis per day, more specifically several per day, most preferably hundreds per day.

The method of the present invention allows analyzing the effect of drug candidates on protein complexes in samples both purified or crude, i.e. biological samples, which may or may not have undergone some purification but still may contain extraneous contaminants, with high accuracy, high sensitivity and high signal-to-noise ratio. Thus the effect of drug candidates on high molecular weight protein complexes from contaminated samples, which are otherwise difficult to analyze due to the presence of mixtures, contaminants, or impurities, is made possible by the method of the present invention and further may be made amenable to automation as desired in large-scale processes. This may include the use of software for interpretation of the data as well as robotics for the control of the sample preparation and/or analysis.

The present invention further provides the use of this method in various applications such as product development, optimization of lead compounds, in manufacturing processes, including automated and/or high throughput applications.

In practicing an embodiment of the method of the present invention, a drug candidate is incubated with a sample containing a protein complex to be analyzed. After incubation, the sample is first subjected to cross-linking conditions using e.g. amine reactive cross-linking chemical reactions for stabilizing the protein complex prior to high mass MALDI mass spectrometric analysis. Typical cross-linking reagents useful for the method of the invention are such reagents as listed in patent application WO 2006/116893. Possible cross-linking reagents include both homo- and hetero-multifunctional reagents and comprise imidoesters, N-hydroxysuccinimide (succinimidyl)esters, maleimides, haloacetates, pyridyl disulfides, hydrazides, carbodiimides, aryl azides, isocyanates, vinyl sulfones, and the like. Illustrative of the crosslinking reaction of a succinimidyl ester is the scheme below, wherein R is a residue comprising a further reactive group, e.g. another succinimidyl ester function or a residue bearing iodine, and $R'-NH_2$ indicates an accessible amino group in the protein:

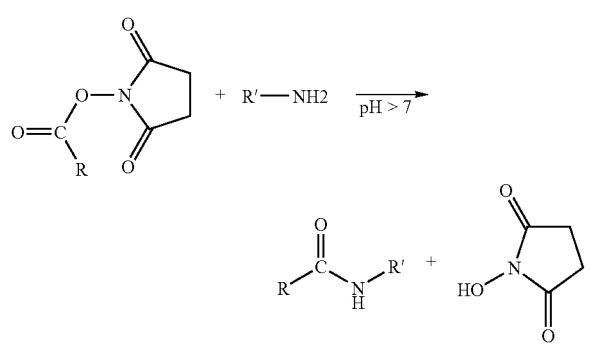

Typically, a solution containing a cross-linking reagent of choice is added to a sample containing the protein complex target and the drug candidate followed by incubation for a specified time, e.g. 1 to 60 minutes, preferably around 45 minutes, at around room temperature, 0° C. or up to 40° C., to ensure completion of the reaction. Typical cross-linkers include homo- and hetero-multifunctional cross-linking agents. Preferred cross-linking reagents for this analysis are mixtures composed of at least one of the following cross-linkers: Disuccinimidyl tartrate, octanedioic acid bis(3-sulfo-N-hydroxysuccinimide)ester, iodoacetic acid N-hxdroxysuccinimide ester, disuccinimidyl 3,3'-dithiopropionate, octanedioic acid di-N-hydroxysuccinimide ester, and ethylene glycol bis(succinimidyl succinate).

After completion of the cross-linking reaction, the obtained liquid mixture is used in a high mass MALDI mass spectrometric set up as described above.

While the effect of drug candidates on protein-protein interactions or protein complexes can be determined in a purified sample, it is also possible to determine this effect in complex biological matrices.

After completion of the cross-linking reaction, the liquid mixture is used in a MALDI MS setup. In a preferred embodiment, an aliquot, e.g. 1 microliter, of the sample containing the now covalently stabilized protein complex together with separate complex subunits is mixed with an aliquot, e.g. 1 microliter, of a matrix solution to obtain a sample/matrix-mixture or spotted directly on a plate covered with a thin layer of a matrix or other MALDI sample deposition techniques, as known by those familiar in the art. On interaction with the matrix solution, the protein complexes are co-crystallized and their composition frozen for the purposes of mass spectrometric analysis. Typical matrix solutions for use in the methods disclosed herein have a sufficient absorption at the wavelength of the laser to be used in performing desorption and ionization, are liquid at around room temperature (25° C.) and can form a vitreous or glassy solid. Among the preferred matrices are those mentioned to be preferred in patent application WO 2006/116893. Particularly preferred is sinapinic acid (3-(4-hydroxy-3,5-dimethoxyphenyl)-prop-2-enoic acid). Materials of relatively low volatility are preferred to avoid rapid evaporation under conditions of vacuum during MS analyses. Preferably the liquid has an appropriate viscosity to facilitate dispensing of microliter to nanoliter volumes of matrix, either alone or mixed with a sample solution. Preferably, any liquid(s) used in preparation of the solution are removed by drying the sample/matrix-mixture before analysis to form a homogenous "solid solution", i.e. comprising the analyte complexes distributed throughout the matrix. In a preferred embodiment, the matrix solution contains, for example, sinapinic acid (around 10 mg/mL) in a solution containing acetonitrile, water and trifluoroacetic acid. Due to the stabilization of complexes achieved by the crosslinking step it is not necessary to undergo the laborious process of optimizing "soft" conditions such as matrix solutions without organic solvent or soft laser analysis (i.e. low laser powers used or first shot analysis).

While the above described preferred embodiment involves using dried liquid solutions, other methods such as liquid MALDI, online AP-MALDI, solid phase preparation, and other sample preparation techniques can be used as they are well known in the art.

In a preferred embodiment, the ion particles generated are extracted for analysis by the mass analyzer in a delayed fashion prior to separation and detection in a mass analyzer. Preferably, the separation formats include, but are not limited to, linear or reflectron time-of-flight (ToF), with linear and nonlinear fields, for example, curved field reflectron; single or multiple quadrupole; single or multiple magnetic or electric sector; Fourier transform ion cyclotron resonance (FTICR); or ion trap mass spectrometers; most preferably linear time-of-flight (ToF).

While a ion conversion dynode (ICD) is preferred, other known detectors, which are sensitive to high mass ions and thus are able to detect chemically stabilized multi-component ions, may be used, which include, but are not limited to, superconducting tunnel junction (STJ) detectors, optically decoupled, amplified, or specially coated electron multipliers or MCP's, and other cryodetectors or sensitive high mass detectors, as they are well known in the art.

EXAMPLES

Mass Spectrometry: All the mass measurements were performed on MALDI ToF mass spectrometer Reflex IV (Bruker, Bremen) equipped with a high mass retrofit detector system (HM1, CovalX, Zürich, Switzerland). CovalX HM1 high mass retrofit system is designed to optimize the detection of high molecular weight molecular ions in the 5-1500 kDa range. CovalX HM1 high mass retrofit system can be installed on every standard MALDI-TOF mass spectrometer.

Example 1

Use of Chemical Crosslinking and High Mass MALDI Mass Spectrometry for the Determination of the Effect of AG32 on Thymidin Kinase Protein Complex AG32 is a drug candidate targeting the enzyme Thymidin Kinase (TK). This drug candidate is belonging to the lamotrigine coumpounds family with a MW of around 400 Da. This enzyme catalyze the transfer of γ-phosphate from ATP to the 5' OH group of thymidine, yielding thymidine monophosphate, a precursor for DNA synthesis in the so-called pyrimidine salvage pathway. This enzyme is essential for a large number of virus pathogenicity, especially for the reactivation of viruses from latency.

Figure 2:
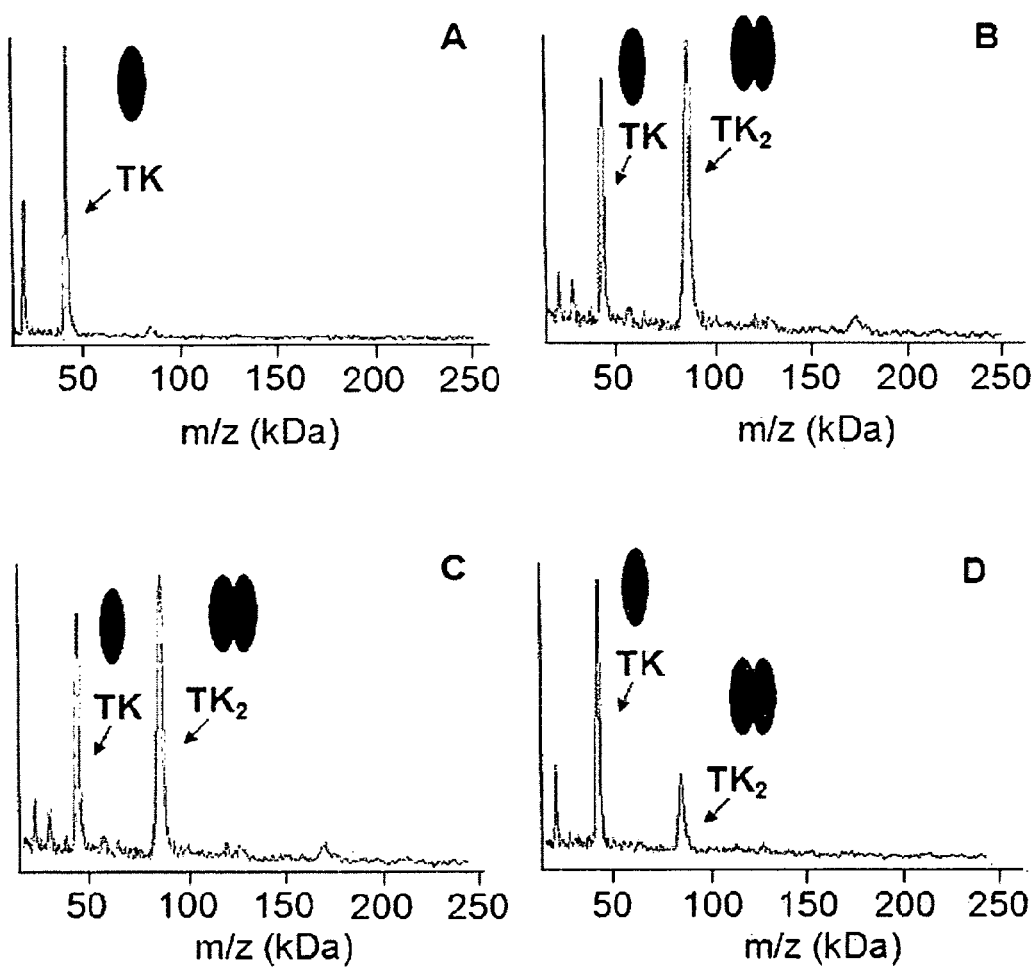
FIG. 2: Effect of AG32 on Thymidin Kinase protein complex. A purified sample of the protein complex Thymidin Kinase is directly analyzed by high-mass MALDI mass spectrometry before (A) and after cross-linking (B). Purified sample of Thimidin Kinase are incubated with a negative control molecule AG0 (C) or with the drug candidate AG32 (D) and subsequently cross-linked and analyzed by high-mass MALDI ToF mass spectrometry.

Purified samples of TK are prepared and submitted to cross-linking using a mixture of 1:1:1 disuccinimidyl 3,3'-dithiopropionate, disuccinimidyl glutarate, and octanedioic acid bis(3-sulfo-N-hydroxysuccinimide)ester (100 mg/ml). Before (FIG. 2A) and after incubation at 25° C. for 45 min with the cross-linking reagent, the sample is directly analyzed using high-mass MALDI ToF mass spectrometry (FIG. 2B). Purified samples of Thymidin Kinase are incubated 1 hour with a negative control molecule (10 μM, AG0, having similar molecular weight of the drug candidates) (FIG. 2C), or with a drug candidate (AG32, 10 μM) (FIG. 2D). After incubation, the samples are submitted to the cross-linking reagent as described above for 45 minutes at 25° C. Then the samples are directly analyzed by high-mass MALDI ToF mass spectrometry. After the mass spectrometric analysis, the mass peak area of the peak corresponding to the TK complex is estimated for the negative control and for the AG32 experiment. With the negative control molecule, no difference is detected on the mass peak area of the peak corresponding to TK complex. After incubation with AG32, the mass peak area of the peak corresponding to TK is lower showing that AG32 has a disruptive effect on TK complex. The protein concentration for each sample is 1 μM with a volume of 10 μL. 1 μL of the drug candidate solution (100 μM) is mixed with the protein sample for 1 hour incubation time at 25° C. 1 μL of 1 mg/mL crosslinking mixture is used to stabilize the protein complex before high mass MALDI ToF analysis. Samples are prepared by mixing 1 μL of protein complex solution with 1 μL of sinapic acid (10 mg/mL in 70% acetonitrile:30% water:0.1% trifluoroacetic acid) and spotting 1 μL using dried droplet technique.

Example 2

Figure 3:
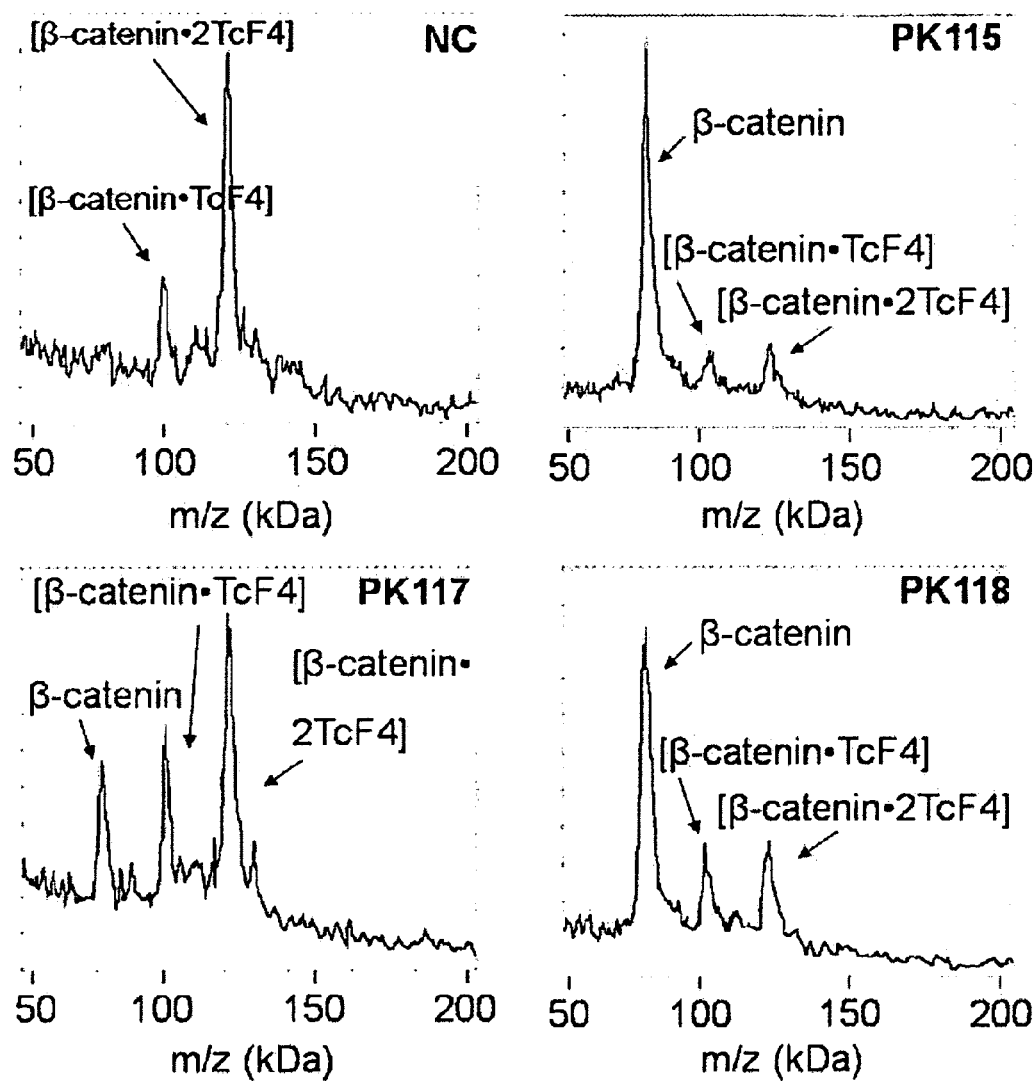
FIG. 3: Effect of PK115, PK117 and PK118 on the protein complex Tcf4/β-catenin. Protein complex Tcf4/β-catenin is incubated with a negative control molecule (NC); PK115, PK117 and PK118. After incubation, the samples are submitted to the cross-linking protocol and analyzed by high-mass MALDI ToF mass spectrometry.

Use of Chemical Cross-linking and High Mass MALDI Mass Spectrometry for the Determination of the Effect of PK115, PK117 and PK118 on the Protein Complex Tcf4/β-catenin Key molecular lesions in colorectal and other cancers cause β-catenin-dependant transactivation of T cell factor (Tcf)-dependant genes. Disruption of this signal represents an opportunity for rational cancer therapy. PK115, PK117 and PKF118 are drug candidates coming from a natural compounds library with MW in the 500 Da range that are targeting the interaction Tcf4/β-catenin. Purified samples of Tcf4/β-catenin complex are incubated (1 hour, 25° C.) with a negative control molecule (NC) (having similar MW and chemical structure of drug candidates) or with the drug candidates PKF115, PK117 or PK118. After incubation, the samples are submitted to cross-linking using a mixture of 1:1:1 disuccinimidyl 3,3'-dithiopropionate, disuccinimidyl glutarate, and octanedioic acid bis(3-sulfo-N-hydroxysuccinimide)ester (100 μg/ml). After incubation at 25° C. for 45 min with the cross-linking reagent, the samples are directly analyzed using high-mass MALDI ToF mass spectrometry. After the mass spectrometric analysis, the mass peak area of the peak corresponding to Tcf4/β-catenin complex is estimated from the negative control experiment (FIG. 3 NC), from PK115 (FIG. 3 PK115), PK117 (FIG. 3 PK117) and PK118 (FIG. 3 PK117) experiments. After incubation with PK115, PK117 and PK118 the mass peak area of the peak corresponding to Tcf4/β-catenin is lower than for the negative control showing that these drug candidates have a disruptive effect on the Tcf4/β-catenin complex. The protein concentration for each sample is 1 μM with a volume of 10 μL. 1 μL of the drug candidate solution (100 μM) is mixed with the protein sample for 1 hour incubation time at 25° C. 1 μL of 1 mg/mL crosslinking mixture is used to stabilize the protein complex before high mass MALDI ToF analysis. Samples are prepared by mixing 1 μL of protein complex solution with 1 μL of sinapic acid (10 mg/mL in 70% acetonitrile:30% water:0.1% trifluoroacetic acid) and spotting 1 μL using dried droplet technique.

Example 3

Quantitative Analysis of Nutlin-3a and Nutlin-3b Inhibition of MDM2-p53 Interaction MDM2 and p53 are two proteins involved in a major pathway protecting cells from malignant transformation. In response to stress, the cellular level of p53 is elevated by a posttranslational mechanism, leading to cell cycle arrest or apoptosis. Under non-stressed conditions, p53 tightly interact with MDM2 protein. As MDM2 blocks the ability of p53 to induce cell cycle arrest, the interaction MDM2-p53 is considered as a potential target for cancer therapy. Nutlin-3a and Nutlin-3b have been identified as inhibitors of the interaction allowing activation of apoptosis in the cells treated. The $IC_{50}$ of these two inhibitors have been determined using Surface Plasmon Resonance with respective values of 0.09 μM for Nutlin-3a and 13.6 μM for Nutlin-3b (Vassilev, L. T. et al., Science 403:844-846, 2004). In the following, it is demonstrated how $IC_{50}$ values of Nutlin-3a and Nutlin-3b inhibition of MDM2-p53 interaction are determined with high accuracy.

MDM2 (2 μM, 5 μL) is incubated for 60 min with different concentration of Nutlin-3a or Nutlin-3b (from 0.01 μM to 100 μM). After incubation, the sample is mixed with p53 (2 μL) and submitted to cross-linking using a mixture of 1:1:1 disuccinimidyl 3,3'-dithiopropionate, disuccinimidyl glutarate, and octanedioic acid bis(3-sulfo-N-hydroxysuccinimide)ester (100 μg/mL). After incubation at 25° C. for 45 min with the cross-linking reagent, the samples are directly analyzed using high-mass MALDI ToF mass spectrometry (FIG. 4C, D, E). From the mass spectra, the mass peak area of the protein complex MDM2-p53 when incubated with the different concentration of Nutlin-3a or Nutlin-3b is estimated. From the mass peak area value it is possible to estimate the percentage of protein complex still present in solution. By plotting this percentage as a function of the concentration of inhibitors present in the sample (log scale), it is possible to determine the $IC_{50}$ value for Nutlin-3a and Nutlin-3b. The values determined (70 nM for Nutlin-3a and 15.4 µM for Nutlin-3b) are close to the value already published with other methodologies such as Surface Plasmon Resonance (Vassiley et al., loc. cit.).

For the determination of inhibition of the MDM2-p53 interaction by another drug candidate, the protein concentration for each sample is 2 µM with a total volume of 10 µL. 1 µL of the drug candidate solution (from 0.1 to 100 µM) is mixed with the MDM2 protein sample for 1 hour incubation time at 25° C., and then mixed with p53 (2 µM, 5 µL). 1 µL of 1 mg/mL cross-linking mixture is used to stabilize the protein complex before high mass MALDI ToF analysis. Samples are prepared by mixing 1 µL of protein complex solution with 1 µL of sinapic acid (10 mg/mL in 70% acetonitrile:30% water: 0.1% trifluoroacetic acid) and spotting 1 µL using dried droplet technique.

The invention claimed is:

1. A method for determining the effect of a drug candidate on a protein complex comprising the steps of:
    (a) incubating the drug candidate with the targeted protein complex;
    (b) contacting the sample containing the targeted protein complex and the drug candidate with a cross-linking reagent or a cross-linking reagent mixture to form a covalently stabilized protein complex;
    (c) analyzing the intact ions formed from the protein complex of step (b) by MALDI ToF mass spectrometry equipped with a high mass detector;
    (d) determining directly the effect the drug candidate on the protein complex by comparing the mass peak area corresponding to the protein complex after incubation with the drug candidate with the mass peak area of the same protein complex after incubation with a negative control molecule.

2. The method of claim 1, wherein steps (a) to (d) are performed in parallel with different concentrations of the drug candidate in step (a), the effects quantified in step (d), and represented as a function of drug candidate concentration.

3. The method of claim 2, wherein the effects quantified in step (d) are represented as an $IC_{50}$ value of the drug candidate for the targeted protein complex.

4. The method of claim 1, comprising the steps of:
    (a) obtaining a first sample by incubating the drug candidate or the negative control molecule with a targeted protein complex;
    (b) contacting said first sample with a cross-linking reagent or a cross-linking reagent mixture to obtain a second sample comprising the covalently stabilized protein complex,
    (c) mixing said second sample with a matrix solution to obtain a sample/matrix mixture;
    (d) depositing said sample/matrix mixture on a substrate, thereby forming a homogeneous, thin layer;
    (e) illuminating the sample/matrix mixture with radiation from a laser whereby said protein complex covalently stabilized is desorbed and intact ions are generated;
    (f) mass separating and detecting said intact ions of the undigested, unfragmented covalently stabilized protein complex using a mass separation and a high mass detection system;
    (g) determining the mass peak area of the peaks measured for the protein complex detected;
    (h) comparing the value for the mass peak area of the peak corresponding to the protein complex obtained after incubation of the protein complex with the drug candidate with the value for the mass peak area of the peak corresponding to the protein complex obtained after incubation with the negative control molecule;
    (i) determining from the comparison the effect of the drug candidate on the targeted protein complex.

5. The method of claim 3, comprising the steps of:
    (a) incubating a targeted protein complex sample with several different concentrations of a drug candidate and a negative control molecule;
    (b) contacting said first series of samples from step (a) with a cross-linking reagent or cross-linking reagent mixture to obtain a second series of samples containing the covalently stabilized protein complex,
    (c) mixing said second series of samples from step (b) with a matrix solution to obtain a sample/matrix mixture;
    (d) depositing said sample/matrix mixtures on a substrate, thereby forming a homogeneous, thin layer;
    (e) illuminating the sample/matrix mixtures with radiation from a laser whereby said protein complex covalently stabilized is desorbed and intact ions are generated;
    (f) mass separating and detecting said intact ions of the undigested, unfragmented covalently stabilized protein complex using a mass separation and a high mass detection system;
    (g) determining the mass peak area of the peaks measured for the protein complex detected;
    (h) comparing the value for the mass peak area of the peak corresponding to the protein complex obtained after incubation of the protein complex with different concentrations of the drug candidate with the value for the mass peak area of the peak corresponding to the protein complex obtained after incubation with the negative control molecule;
    (i) determining from the comparison the percentage of protein complex having been present after incubation in step (a),
    (j) determining the $IC_{50}$ value of the drug candidate against the target by plotting the percentage determined in step (i) as a function of the concentration of the drug candidate.

6. The method according to claim 1, wherein the comparison of the mass peak area corresponding to the protein complex after incubation with the drug candidate with the mass peak area of the same protein complex after incubation with a negative control molecule is used to select and rank a large number of drug candidates for their effect on the targeted protein complex.

7. The method according to claim 1, wherein the effect of the drug candidate on the protein complex is established based on the total mass peak area of the peaks corresponding to the protein complex and corresponding to the complex subunits in the same mass spectrometry spectrum.

8. The method according to claim 1, wherein the effect of the drug candidate on the protein complex is analyzed in purified multicomponent samples or in heterogeneous biological matrices.

9. The method according to claim 1, wherein the drug candidate is a small molecule, an antibody, an antibody fragment, a therapeutic protein or a therapeutic peptide.

10. The method according to claim 1, wherein the cross-linking reagent is one reagent or a mixture of cross-linking reagents selected from the group consisting of disuccinimidyl tartrate, octanedioic acid bis(3-sulfo-N-hydroxysuccinimide) ester, iodoacetic acid N-hxdroxysuccinimide ester, di succinimidyl 3,3'-dithiopropionate, octanedioic acid di-N-hydroxysuccinimide ester, disuccinimidyl glutarate, and ethylene glycol bis(succinimidyl succinate).

11. The method according to claim 1, wherein the high mass detector is an ion conversion dynode detector.

12. The method according to claim 1, for use in lead compound optimization, characterization of drug candidates in drug development processes, manufacturing processes and quality control processes.

13. The method according to claim 1, for use in automated high throughput applications.

* * * * *